United States Patent
Zhan et al.

(10) Patent No.: US 11,680,718 B2
(45) Date of Patent: Jun. 20, 2023

(54) BASE AND HUMIDIFIER

(71) Applicant: SHENZHEN CHENBEI TECHNOLOGY CO., LTD., Shenzhen (CN)

(72) Inventors: Xuequn Zhan, Shenzhen (CN); Jinlong Huang, Shenzhen (CN)

(73) Assignee: SHENZHEN CHENBEI TECHNOLOGY CO., LTD., Shenzhen (CN)

( * ) Notice: Subject to any disclaimer, the term of this patent is extended or adjusted under 35 U.S.C. 154(b) by 141 days.

(21) Appl. No.: 17/314,689

(22) Filed: May 7, 2021

(65) Prior Publication Data
US 2021/0404676 A1    Dec. 30, 2021

(30) Foreign Application Priority Data

Jun. 30, 2020  (CN) .......................... 202010616989.4

(51) Int. Cl.
| | |
|---|---|
| *F24F 6/12* | (2006.01) |
| *F24F 11/52* | (2018.01) |
| *F24F 110/20* | (2018.01) |
| *F24F 110/10* | (2018.01) |
| *F24F 6/00* | (2006.01) |
| *A61L 9/12* | (2006.01) |

(52) U.S. Cl.
CPC ................ *F24F 6/12* (2013.01); *F24F 11/52* (2018.01); *A61L 9/122* (2013.01); *F24F 2006/008* (2013.01); *F24F 2110/10* (2018.01); *F24F 2110/20* (2018.01)

(58) Field of Classification Search
CPC ........ F24F 6/12; F24F 11/52; F24F 2006/008; F24F 2110/10; F24F 2110/20; F24F 8/50; F24F 11/64; F24F 11/72; F24F 11/89; F24F 13/06; F24F 13/32; A61L 9/122; A61L 9/12
See application file for complete search history.

(56) References Cited

U.S. PATENT DOCUMENTS

| | | | | |
|---|---|---|---|---|
| 4,643,351 A | * | 2/1987 | Fukamachi | ......... B01F 23/2133 236/44 E |
| 4,752,422 A | * | 6/1988 | Uchida | ..................... A61L 9/14 261/DIG. 65 |
| 5,464,572 A | * | 11/1995 | Bonzi | ....................... F24F 3/16 361/231 |

(Continued)

*Primary Examiner* — Stephen Hobson
(74) *Attorney, Agent, or Firm* — Anova Law Group, PLLC

(57) ABSTRACT

A base of a humidifier includes a housing, an air outlet assembly, and a first partition. The housing includes a receiving chamber, a first air inlet, and a second air inlet. The air outlet assembly is disposed in the receiving chamber and includes a fan, a temperature and humidity sensor, and an aroma component. The first partition is disposed in the receiving chamber and configured to spatially separate the temperature and humidity sensor from the fan and the aroma component. The fan is configured to introduce a first airflow from the first air inlet to pass through the temperature and humidity sensor, and reach the fan; introduce a second airflow flow from the second air inlet to pass through the aroma component without passing through the temperature and humidity sensor, and reach the fan; and discharge the first second airflow out of the receiving chamber through the air outlet.

20 Claims, 9 Drawing Sheets

(56) References Cited

U.S. PATENT DOCUMENTS

| | | | | |
|---|---|---|---|---|
| 5,611,967 A * | 3/1997 | Jane | ............... | B01F 23/215 |
| | | | | 261/142 |
| 6,089,548 A * | 7/2000 | Pfitzner | ............... | B01D 1/00 |
| | | | | 261/142 |
| 6,196,527 B1 * | 3/2001 | Huang | ............... | F24F 6/18 |
| | | | | 261/DIG. 65 |
| 7,011,795 B2 * | 3/2006 | Thompson | ............... | A61L 9/125 |
| | | | | 422/123 |
| 7,677,536 B2 * | 3/2010 | Wang | ............... | A61L 9/03 |
| | | | | 261/DIG. 65 |
| 8,296,993 B2 * | 10/2012 | Modlin | ............... | A01M 29/12 |
| | | | | 43/132.1 |
| 9,423,142 B2 * | 8/2016 | Lee | ............... | F24F 6/043 |
| 10,286,099 B2 * | 5/2019 | Le | ............... | B05B 7/0081 |
| 11,318,219 B1 * | 5/2022 | Lee | ............... | A61L 9/03 |
| 2011/0221078 A1 * | 9/2011 | Lev | ............... | F24F 6/12 |
| | | | | 261/DIG. 89 |
| 2012/0261484 A2 * | 10/2012 | Blaylock | ............... | A61L 9/14 |
| | | | | 239/338 |
| 2014/0217623 A1 * | 8/2014 | Franks | ............... | A61K 35/30 |
| | | | | 29/428 |
| 2014/0369896 A1 * | 12/2014 | Franks | ............... | A61L 9/122 |
| | | | | 422/124 |
| 2016/0030620 A1 * | 2/2016 | Peterson | ............... | A61L 9/042 |
| | | | | 261/84 |
| 2017/0232130 A1 * | 8/2017 | Conroy | ............... | G06Q 10/08 |
| | | | | 422/4 |
| 2018/0290157 A1 * | 10/2018 | Gruenbacher | ............... | B05B 1/267 |
| 2019/0083671 A2 * | 3/2019 | McDonnell | ............... | F24F 6/12 |
| 2019/0085852 A1 * | 3/2019 | Brown | ............... | G05D 1/0011 |
| 2019/0195528 A1 * | 6/2019 | Puranen | ............... | F24F 11/81 |
| 2020/0147257 A1 * | 5/2020 | Chiu | ............... | A61L 9/14 |
| 2020/0278128 A1 * | 9/2020 | Patel | ............... | F24F 1/0375 |
| 2021/0190342 A1 * | 6/2021 | Zhan | ............... | F24F 6/12 |
| 2022/0316721 A1 * | 10/2022 | Tanaka | ............... | F24F 6/08 |
| 2022/0316772 A1 * | 10/2022 | Wu | ............... | F24F 11/64 |

* cited by examiner

BASE AND HUMIDIFIER

CROSS-REFERENCE TO RELATED APPLICATION

This application claims priority to Chinese Patent Application No. 202010616989.4, filed on Jun. 30, 2020, the entire content of which is incorporated herein by reference.

TECHNICAL FIELD

The present disclosure relates to the field of humidifiers, and more specifically, to a base and a humidifier.

BACKGROUND

A humidifier can decompose water molecules and dissolved plant essential oils into nano-scale cold mist with a diameter of 0.1-5 microns by using high-frequency vibration generated by an ultrasonic vibration device, and the cold mist is dispersed in the surrounding air, filling the air with fragrance and increasing the air humidity.

Nowadays, humidifiers are gradually integrated into people's daily life. An aroma humidifier in conventional technology generally has a base, and the intake air flows through a temperature and humidity sensor when passing through the aroma component. Since the temperature and humidity of the air perfumed by the aroma component is quite different from the air without passing through the aroma component, the detection of the temperature and humidity of the air of the environment is not accurate if air sample is coming from the aroma component. The disclosed device are directed to solve at least the inaccuracy problems set forth above.

SUMMARY

One aspect of the present disclosure provides a base. The base includes a housing, an air outlet assembly, and a first partition. The housing includes a receiving chamber, a first air inlet, and a second air inlet. The air outlet assembly is disposed in the receiving chamber and includes a fan, a temperature and humidity sensor configured to measure a first airflow introduced from the first air inlet, and an aroma component configured to aromatize a second airflow introduced from the second air inlet. The first partition is disposed in the receiving chamber and configured to spatially separate the temperature and humidity sensor from the fan and the aroma component. The fan is configured to introduce the first airflow from the first air inlet to pass through the temperature and humidity sensor, flow through a ventilation opening at the first partition, and reach the fan; introduce the second airflow flow from the second air inlet to pass through the aroma component without passing through the temperature and humidity sensor, and reach the fan; and discharge the first airflow and the second airflow out of the receiving chamber through the air outlet Another aspect of the present disclosure provides a humidifier. The humidifier includes: a water tank, a misting assembly, and a base. The water tank includes a water storage tank, a mist outlet channel, a mist outlet, and a water outlet. The base includes a housing, an air outlet assembly, and a first partition. The housing includes a receiving chamber, a first air inlet, and a second air inlet. The air outlet assembly is disposed in the receiving chamber and includes a fan, a temperature and humidity sensor configured to measure a first airflow introduced from the first air inlet, and an aroma component configured to aromatize a second airflow introduced from the second air inlet. The first partition is disposed in the receiving chamber and configured to spatially separate the temperature and humidity sensor from the fan and the aroma component. The fan is configured to introduce the first airflow from the first air inlet to pass through the temperature and humidity sensor, flow through a ventilation opening at the first partition, and reach the fan; introduce the second airflow flow from the second air inlet to pass through the aroma component without passing through the temperature and humidity sensor, and reach the fan; and discharge the first airflow and the second airflow out of the receiving chamber through the air outlet. The water tank is configured to be detachably mounted to the base. The mist outlet channel, the mist outlet and the air outlet are connected. The water storage chamber of the housing is connected to the mist outlet channel of the water tank and the air outlet of the base, and is connected to the water storage tank through the water outlet. The misting assembly is positioned in the receiving chamber and configured to atomize water stored in the water storage chamber.

Other aspects of the present disclosure can be understood by those skilled in the art in light of the description, the claims, and the drawings of the present disclosure.

BRIEF DESCRIPTION OF THE DRAWINGS

In order to illustrate the technical solutions in accordance with the embodiments of the present disclosure more clearly, the accompanying drawings to be used for describing the embodiments are introduced briefly in the following. It is apparent that the accompanying drawings in the following description are only some embodiments of the present disclosure. Persons of ordinary skill in the art can obtain other accompanying drawings in accordance with the accompanying drawings without any creative efforts.

Figure 1:
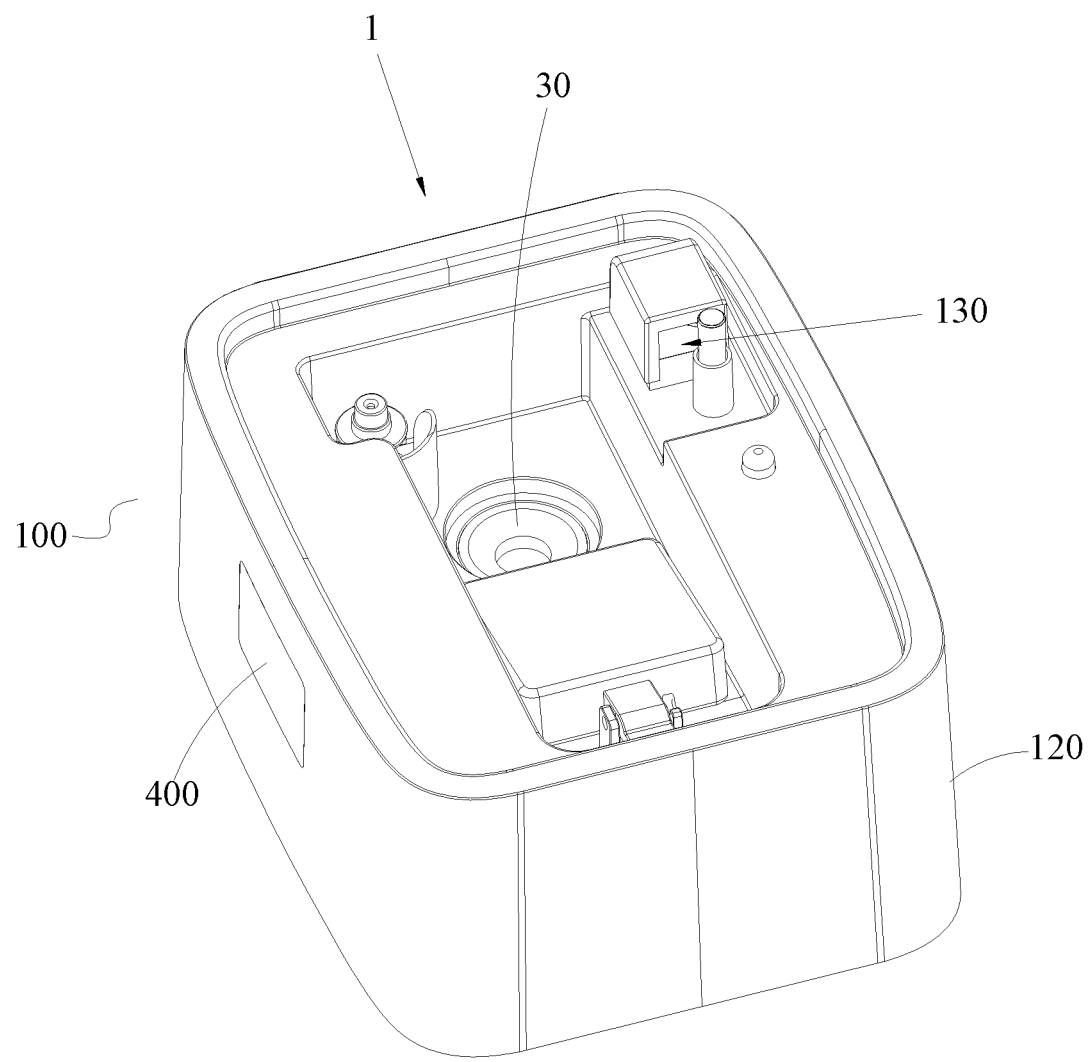
FIG. 1 is a schematic diagram of an overall structure of a base according to an embodiment of the present disclosure.

Reference numerals: Base 1; Housing 100; Receiving chamber 110; Upper housing 120; First partition 121; Ventilation hole 1210; Second partition 122; First flow channel 123; Second flow channel 124; Accommodating chamber 125; Air outlet 130; Bottom cover 140; First air inlet 141; Second air inlet 142; First guiding plate 150; Second guiding plate 160; Water storage chamber 170; Air outlet assembly 200; Fan 210; Air outlet pipe 211; Temperature and humidity sensor 220; Aroma component 230; First control board 310; Second control board 320; Display device 400; Humidifier 2; Water tank 20; Mist outlet 21; Water storage tank 22; Mist outlet channel 23; Water outlet 24; Misting assembly 30.

DETAILED DESCRIPTION OF THE EMBODIMENTS

Technical solutions of the present disclosure will be described in detail with reference to the drawings. It will be appreciated that the described embodiments represent some, rather than all, of the embodiments of the present disclosure. Other embodiments conceived or derived by those having ordinary skills in the art based on the described embodiments without inventive efforts should fall within the scope of the present disclosure.

It should be noted that, when one component is referred to as being "fixed to" another component, it may be directly set on another component or it is also possible that there is an intermediate component between them. When one component is referred to as being "disposed on" another component, it may be directly disposed on the other component or it is possible that there is a third component between them. When one component is referred to as being "connected to" another component, it may be directly connected to the other component or it is possible that there is an intermediate component between them.

In the specification, unless specified or limited otherwise, terms such as "length", "width", "front", "rear", "right", "left", "inner", "outer", "lower", "upper", "horizontal", "vertical", "above", "below", "up", "top", "bottom", "inner", "outer" should be construed as referring to the orientation or position as then described or as shown in the drawings under discussion. These terms are for convenience of description and do not require a corresponding device or component to be constructed or operated in a particular orientation, and is not considered as limiting the disclosed invention.

In addition, terms such as "first" and "second" are used herein for purposes of description and are not intended to indicate or imply relative importance or significance. Thus, features limited by "first" and "second" are intended to indicate or imply including one or more than one of these features. In the description of the present disclosure, "a plurality of" relates to two or more than two.

Figure 2:
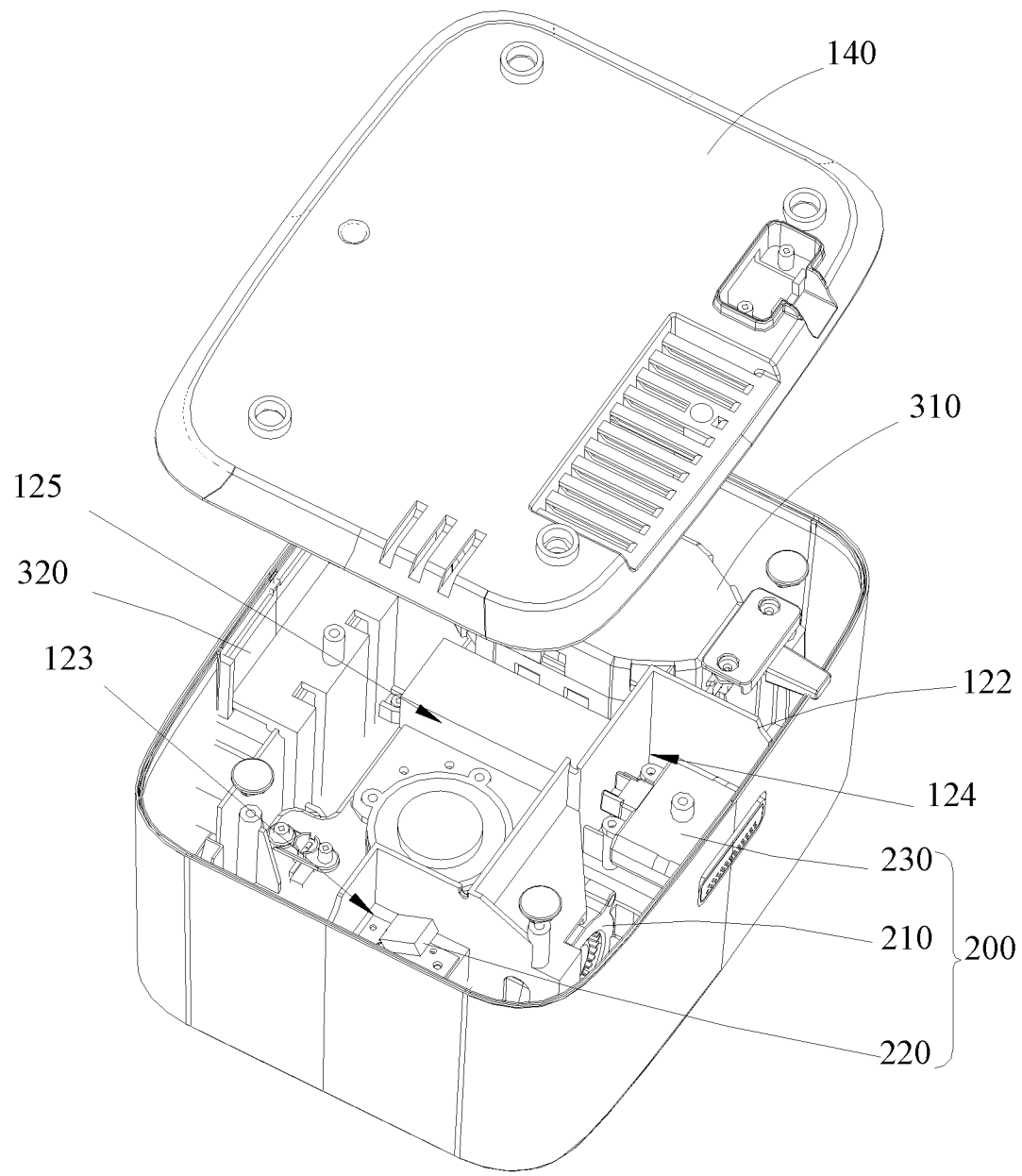
FIG. 2 is an exploded schematic diagram of the base according to an embodiment of the present disclosure.
Figure 3:
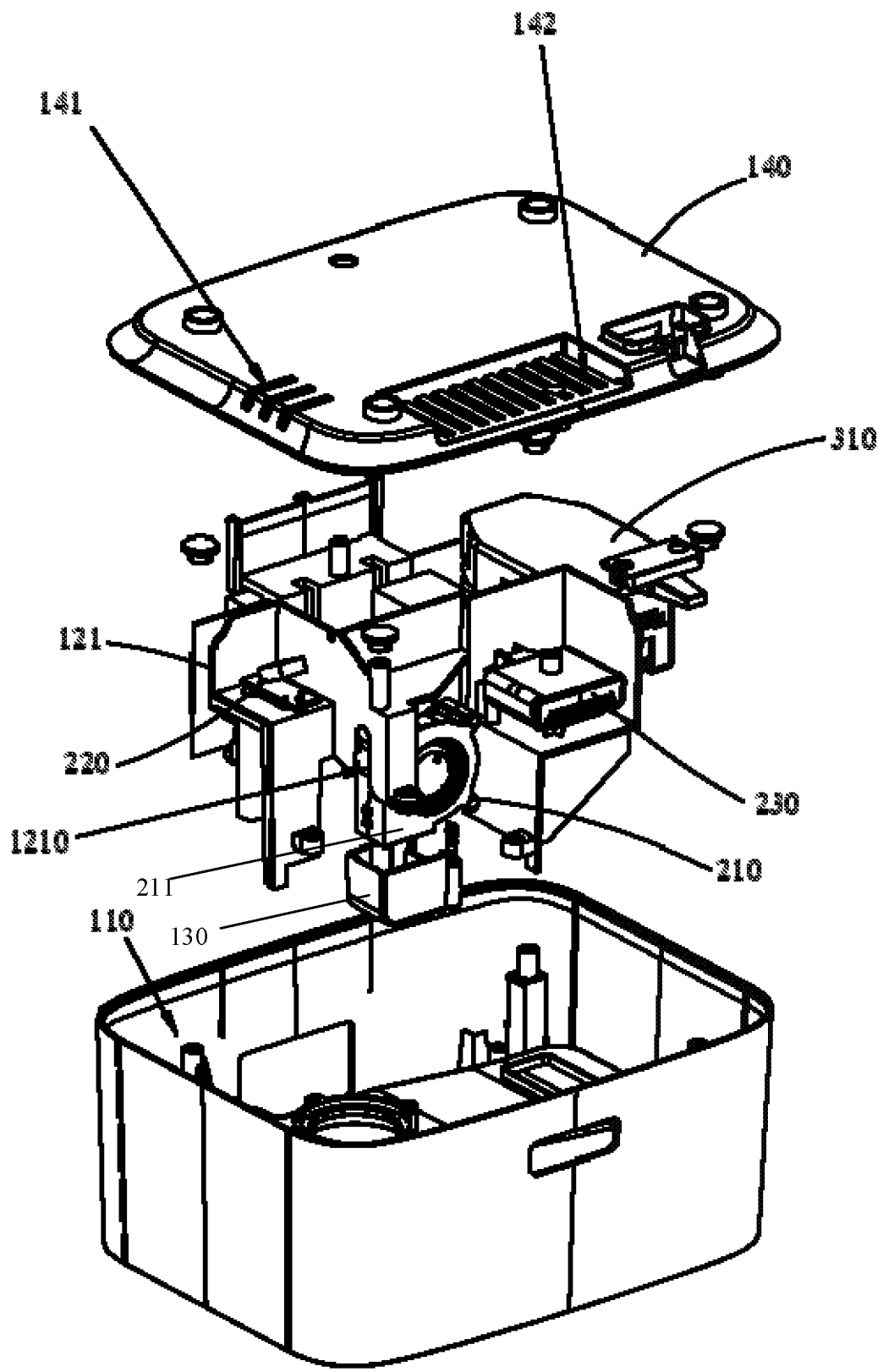
FIG. 3 is another exploded schematic diagram of the base according to an embodiment of the present disclosure.

Referring to FIG. 1 to FIG. 3, a base provided in the embodiments of the present disclosure will be described below. A base 1 includes a housing 100 and an air outlet assembly 200. The housing 100 includes a receiving chamber 110, and an air outlet 130 and an air inlet are disposed on the housing 100. The air outlet assembly 200 is disposed in the receiving chamber 110 and includes a fan 210, a temperature and humidity sensor 220, and an aroma component 230. The fan 210 is configured to take in airflow from the air inlet and discharge the airflow out through the air outlet 130. In some embodiments, when the fan 210 is in operation, the airflow flowing through the aroma component 230 does not pass through the temperature and humidity sensor 220. In some embodiments, the air outlet includes a first air inlet 141 and a second air inlet 142. The temperature and humidity sensor 220 is configured to measure a first airflow introduced from the first air inlet 141. The aroma component 230 is configured to aromatize a second airflow introduced from the second air inlet 141. The housing 100 further includes a first partition 121 disposed in the receiving chamber 110 and configured to spatially separate the temperature and humidity sensor 220 from the fan 210 and the aroma component 230. The fan 210 is configured to introduce the first airflow from the first air inlet 141 to pass through the temperature and humidity sensor 220, flow through a ventilation opening at the first partition 121, and reach the fan 210; introduce the second airflow flow from the second air inlet 142 to pass through the aroma component 230 without passing through the temperature and humidity sensor 220, and reach the fan 210; and discharge the first airflow and the second airflow out of the receiving chamber 110 through the air outlet 130. In some embodiments, the fan 210 may be a turbo fan. In some embodiments, the fan 210 may include a first side (e.g., a side facing toward the first partition 121) and a second side (e.g., a side facing toward the aroma component 230) opposite to each other. The fan 210 can take in air from the first side and the second side respectively, and a direction of outgoing air may be perpendicular to a direction of incoming air. For example, when the base is placed on a horizontal ground, the opposite sides of the fan 210 may be the left side and the right side of the fan 210 (e.g., the airflow is incoming to the fan 210 horizontally), and the fan 210 may discharge the air through the top of the fan 210 (e.g., the outgoing air may be discharged along a vertical direction).

The air flow may comply with the following principle. When the fan 210 is started, negative pressure can be formed on the first side and the second side of the fan 210, and the air in an external space (i.e., a space external to the base 1) can enter the receiving chamber 110 from the air inlet disposed on the housing 100. The airflow may pass through the temperature and humidity sensor 220 and the aroma component 230 respectively due to the negative pressure and reach the fan 210, and the airflow may be driven by the fan 210 and discharged out through the air outlet 130.

Compared with the conventional technology, in the base 1 provided by the embodiments of the present disclosure, the fan 210 can introduce airflow from the air inlet and discharge it out through the air outlet 130. In some embodiments, when the fan 210 is in operation, the airflow flowing through the aroma component 230 does not pass through the temperature and humidity sensor 220, thereby improving the detection sensitivity of the temperature and humidity sensor 220.

In one embodiment of the base provided by the present disclosure, the fan 210 may take in a first airflow and a second airflow from the air inlet and discharge the first and second airflows out through the air outlet 130. The direction of the first airflow flowing through the temperature and humidity sensor 220 is different from the direction of the second airflow flowing through the aroma component 230. It should be noted that the first airflow may be an airflow flowing in from the external space and passing through the temperature and humidity sensor 220, and the second airflow may be an airflow flowing in from the external space and passing through the aroma component 230. The difference in directions of the first and second airflows may indicate that the flow direction of the first airflow from the air inlet to the negative pressure origin at the fan 210 is different from the flow direction of the second airflow from the air inlet to the negative pressure origin at the fan 210. In this way, the temperature and humidity sensor 220 can separately detect the temperature and humidity of the first airflow, and the fragrance of the aroma component 230 can only be released to the second airflow. As such, the second airflow may not affect the temperature and humidity of the first airflow, thereby improving the detection accuracy of the temperature and humidity sensor 220.

Referring to FIG. 1 to FIG. 3, in one embodiment of the base provided by the present disclosure, the air inlet includes a first air inlet 141 and a second air inlet 142 that are spaced apart. The first air inlet 141 and the second air inlet 142 are respectively connected to the receiving chamber 110. When the fan 210 is working, the first airflow may flow in from the first air inlet 141 and pass through the temperature and humidity sensor 220 to reach the fan 210 and then be discharged. At the same time, the second airflow may flow in from the second air inlet 142 and pass through the aroma component 230, without passing through the temperature and humidity sensor 220, to reach the fan 210 and then be discharged. The arrangement of the first air inlet 141 and the second air inlet 142 allow the first airflow and the second airflow to be formed with different directions in the receiving chamber 110 when the fan 210 is working, thereby avoiding interference between the first airflow and the second airflow. In addition, compared with a base with one air inlet, the first air inlet 141 and the second air inlet 142 can increase the air intake, improve the detection accuracy of the temperature and humidity sensor 220, and improve the fragrance effect of the aroma component 230.

In some embodiments, a total opening area of the first air inlet 141 is smaller than a total opening area of the second air inlet 142. The first air inlet 141 and the second air inlet 142 may each include multiple openings. In one example, the number of openings of the first air inlet 141 may be smaller than the number of openings of the second air inlet 142. In another example, the cross-sectional area of each opening of the first air inlet 141 may be smaller than the cross-sectional area of each opening of the second air inlet 142.

In one embodiment of the base provided by the present disclosure, the air volume flowed into the first air inlet 141 may be smaller than the air volume flowed into the second air inlet 142. In some embodiments, the distance between the fan 210 and the first air inlet 141 is larger than the distance between the fan 210 and the second air inlet 142. In some embodiments, a total opening area of the first air inlet 141 is smaller than a total opening area of the second air inlet 142. Thus, the air volume into the first air inlet 141 may be smaller than the air volume into the second air inlet 142. Since the accuracy of the temperature and humidity detection is related to the wind speed, if the speed of the air is too high, it may be inconvenient to detect the temperature and humidity, and if the speed is too low, the detection of temperature and humidity may be unstable. Therefore, by making the air volume into the first air inlet 141 smaller than the air volume into the second air inlet 142 and through the arrangement of the first partition 121 to slow the air down, the speed of the air could be maintained at a moderate range when passing through the temperature and humidity sensor 220. The accuracy of the detection by the temperature and humidity sensor 220 can be ensured.

Referring to FIG. 3, in one embodiment of the base provided by the present disclosure, a first partition 121 is disposed in the receiving chamber 110 and is fixedly connected to the housing 100. The first partition 121 is disposed between the temperature and humidity sensor 220 and the fan 210. A ventilation opening is disposed on the first partition 121. The ventilation opening may include a ventilation hole 1210 as shown in FIG. 3 and/or other forms of opening, such as a ventilation channel. The first airflow may flow into the receiving chamber 110 and then flow through the ventilation hole 1210 to reach the fan 210. The first partition 121 and the housing 100 jointly enclose and form a first flow channel 123, and the temperature and humidity sensor 220 is positioned in the first flow channel 123. By disposing the first partition 121 between the fan 210 and the temperature and humidity sensor 220, when the fan 210 introduces the first airflow to the temperature and humidity sensor 220, the speed of the first airflow is neither too fast (e.g., slower than the speed of the second airflow) nor too slow (e.g., the first airflow may be accelerated at the ventilation hole 1210 due to the small diameter of the ventilation hole 1210). At the same time, the air pressure on the side of the first partition 121 facing the temperature and humidity sensor 220 is greater than the air pressure on the side of the first partition 121 facing the fan 210, which on one hand, prevents the backflow of the air on the side of the first partition 121 toward the fan 210 from affecting the accuracy and sensitivity of the temperature and humidity sensor 220, and on the other hand, prevent the fragranced air from corroding the temperature and humidity sensor 220.

Referring to FIG. 2, in one embodiment of the base provided by the present disclosure, a second partition 122 and a control assembly are also disposed in the receiving chamber 110. The second partition 122 is connected to the housing 100 and the first partition 121. The air outlet assembly 200 is disposed on one side of the second partition 122, and the control assembly is disposed on the other side of the second partition 122. The second partition 122 and the housing 100 jointly enclose and form a second flow channel 124. The aroma component 230 and the fan 210 are positioned in the second flow channel 124. In some embodiments, the control assembly includes a first control board 310 configured to perform atomization control on liquid of the humidifier (e.g., water stored in the water storage chamber 170 of the housing 100). In some embodiments, the control assembly may further include a second control board 320 configured to perform display control on a display device 400 of the housing 100.

More specifically, the arrangement of the second partition 122, can prevent the fan 210 from discharging air to the first control board 310 and the second control board 320, and block the mixed airflow from contacting the first control board 310 and the second control board 320. Therefore, humid air may not pass through the first control board 310 and the second control board 320, thereby ensuring that the control assembly would not be short-circuited due to moisture or water accumulation.

Referring to FIG. 1 and FIG. 2, in one embodiment of the base provided by the present disclosure, the housing 100 includes an upper housing 120 and a bottom cover 140 connected to a bottom of the upper housing 120. More specifically, the upper housing 120 can be used to fix the fan 210, the temperature and humidity sensor 220, the aroma component 230, and the control assembly. In addition, the receiving chamber 110 of the upper housing 120 can provide protection to the fan 210, the temperature and humidity sensor 220, the aroma component 230, and the control assembly. The bottom cover 140 can be encapsulated by the upper housing 120 to protect, more effectively, the fan 210, the temperature and humidity sensor 220, the aroma component 230, and the control assembly, and prevent these components from being damaged structurally and from being burned or impaired due to water leakage.

In some embodiments, the cross-sectional shape of the upper housing 120 may be circular, which makes the structure of the housing 100 simple and easy to manufacture.

In some embodiments, the upper housing 120 and the bottom cover 140 can jointly enclose and form the receiving chamber 110. The first partition 121 and the second partition 122 divide the receiving chamber 110 into the first flow channel 123, the second flow channel 124, and an accommodating chamber 125.

The first partition 121 and the housing 100 can jointly enclose and form the first flow channel 123, and the temperature and humidity sensor 220 can be disposed in the first flow channel 123. It can be understood that the first flow channel 123 can guide the first airflow such that the first airflow is introduced from the first air inlet 141 by the fan 210 at a certain speed (e.g., the speed may be 2 m/s to 4 m/s). As such, the temperature and humidity sensor 220 disposed in the receiving chamber 110 can continuously perform measurement on the first airflow, which improves the accuracy of the temperature and humidity detection.

The second partition 122 and the housing 100 can jointly enclose and form the second flow channel 124. The aroma component 230 and the fan 210 can be disposed in the second flow channel 124. It can be understood that the second flow channel 124 can introduce the second airflow from the second air inlet 142 such that the fragrance released by the aroma component 230 can be mixed with the second airflow continuously, which improves the fragrance effect.

The control assembly can be disposed in the accommodating chamber 125. It should be noted that the first partition 121 and the second partition 122 can separate the first airflow from the second airflow, and prevent the first airflow and the second airflow from interfering with each other.

More specifically, the first partition 121 may be L-shaped, and its two extending ends may be respectively connected to two adjacent sides of the upper housing 120, such that the first flow channel 123 can have a straight shape. The upper end of the first partition 121 may be connected to the upper housing 120 and the lower end of the first partition 121 may be connected to the bottom cover 140. The second partition 122 may be L-shaped, and one of its two extending ends may be connected to the first partition 121 and the other one of its two extending ends may be connected to the upper housing 120 such that the second flow channel 124 can have a straight shape. The upper end of the second partition 122 may be connected to the upper housing 120 and the lower end of the second partition 122 may be connected to the bottom cover 140. The fan 210 can be positioned in the second flow channel 124, and the first airflow can enter the second flow channel 124 through the ventilation hole 1210, and be discharged out through the air outlet 130 by using the fan 210.

In some embodiments, the first partition 121 and the second partition 122 may be integrally formed to make the structure more stable.

Referring to FIG. 1 and FIG. 2, in one embodiment of the base provided by the present disclosure, the first air inlet 141 and the second air inlet 142 are both disposed on the bottom cover 140. The first air inlet 141 is disposed on the bottom cover 140 at a position corresponding to the temperature and humidity sensor 220, the second air inlet 142 is disposed on the bottom cover 140 at a position corresponding to the fan 210 and the aroma component 230, and the air outlet 130 is disposed on the upper housing 120. When the air enters, the first airflow and the second airflow may respectively flow into the first air inlet 141 and the second air inlet 142 from the bottom of the base 1. The first airflow and the second airflow may be mixed at the fan 210 in the receiving chamber 110, and then discharged out through the air outlet. In some embodiments, the first airflow and the second airflow may flow from bottom to top.

Figure 5:
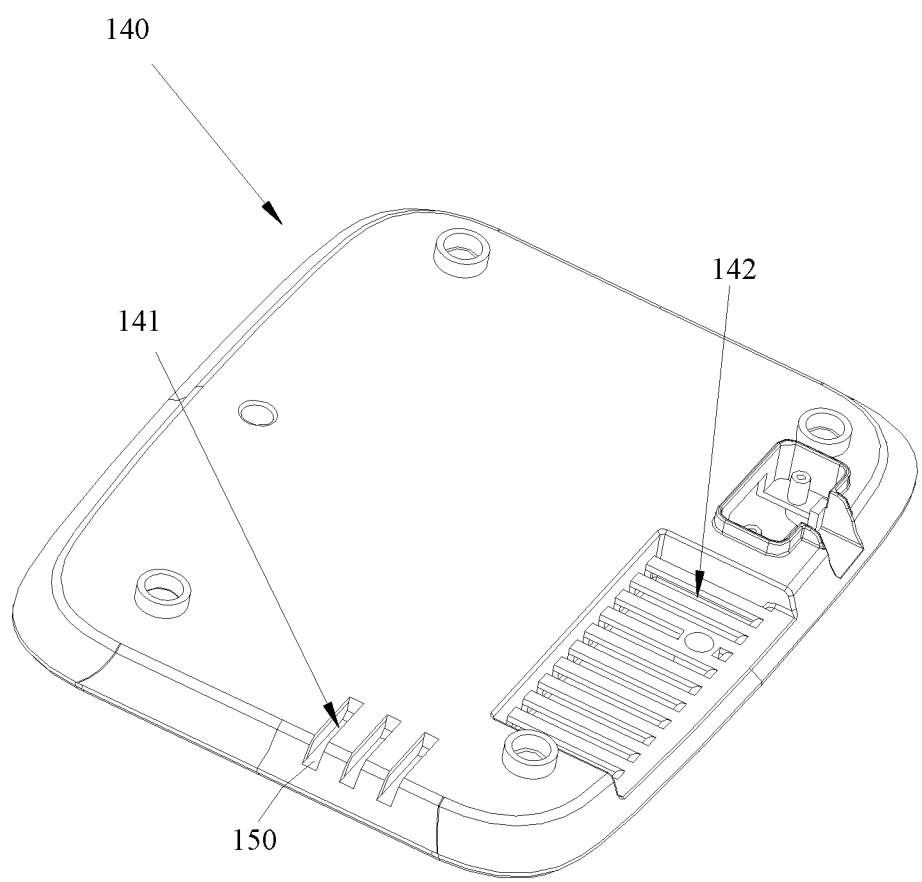
FIG. 5 is a schematic diagram of a back view of a bottom cover according to an embodiment of the present disclosure.
Figure 6:
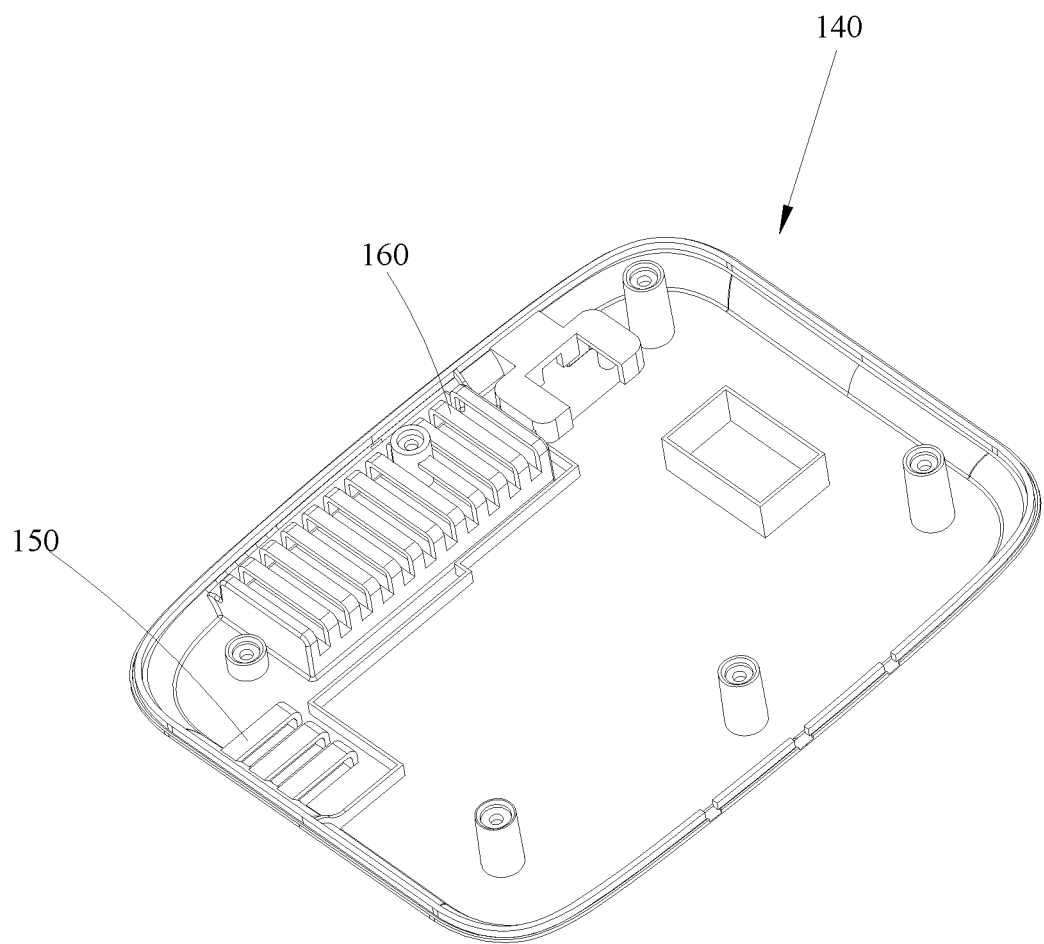
FIG. 6 is a schematic diagram of a front view of the bottom cover according to an embodiment of the present disclosure.

Referring to FIG. 2, FIG. 5, and FIG. 6, in one embodiment of the base provided by the present disclosure, the housing 100 further includes a first guiding plate 150 connected to the bottom cover 140 and recessed at the first air inlet 141, and a second guiding plate 160 connected to the bottom cover 140 and recessed at the second air inlet 142. In one example, the base 1 may include three first air inlets 141, and a first guiding plate 150 is disposed at each first air inlet 141. The first guiding plate 150 can guide the path of the first airflow in the first air inlet into an L shape. The L-shaped path can cause the first airflow to undergo a process of changing direction in the first air inlet 141, such that the large water vapor in the first airflow can drop before the first airflow enters the receiving chamber 110 due to the change of direction and gravity, which can effectively avoid the influence of the water vapor in the first airflow on the electrical performance and accuracy of the detection by the temperature and humidity sensor 220. There are a plurality of second air inlets 142, and a second guiding plate 160 is disposed at each second air inlet 142. The second guiding plate 160 can guide the path of the second airflow in the second air inlet into an L shape, such that the second airflow can undergo a process of changing direction in the second air inlet 142. In this way, the large water vapor in the second airflow can drop before the second airflow enters the receiving chamber 110 due to the change of direction and gravity, which can effectively avoid the influence of the water vapor in the second airflow on the electrical performance and sensitivity of the aroma component 230.

Figure 4:
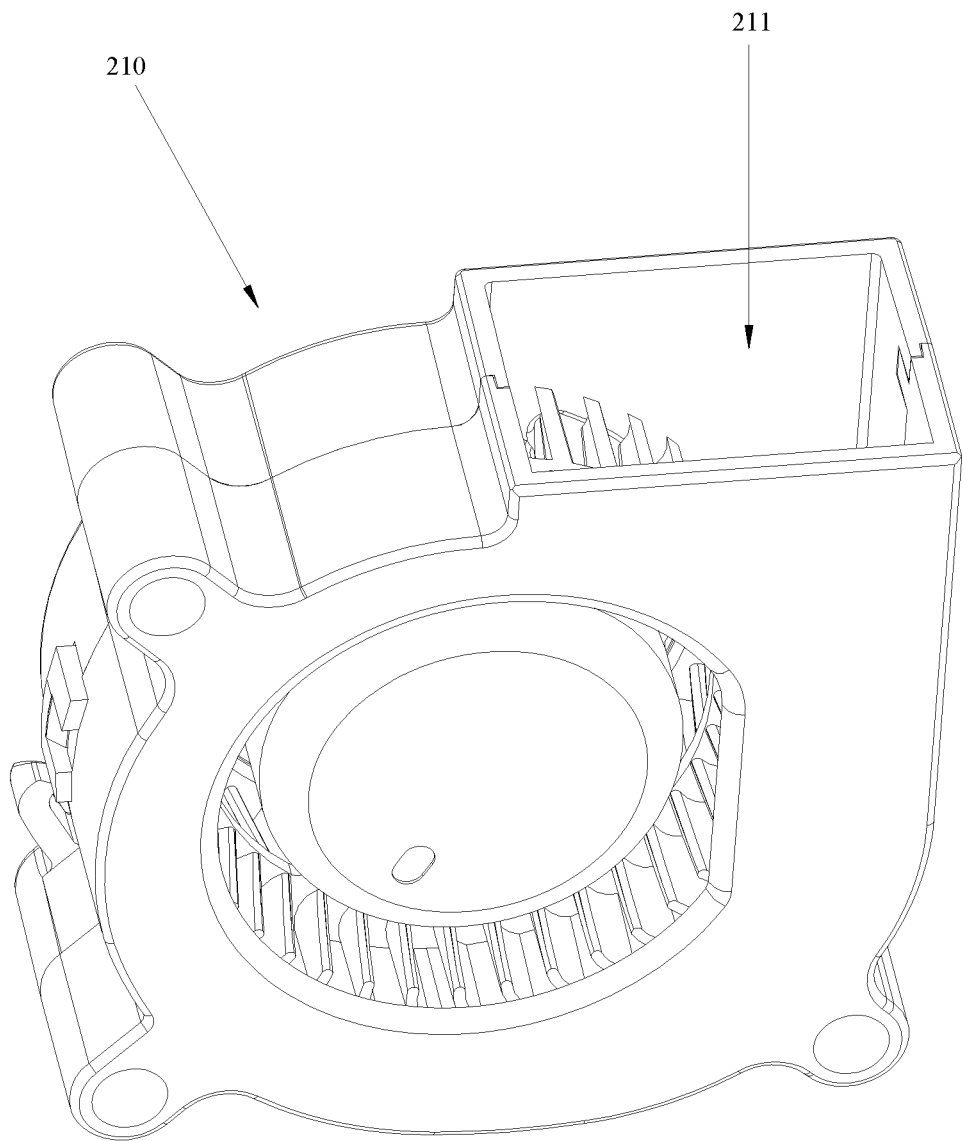
FIG. 4 is a schematic diagram of a fan according to an embodiment of the present disclosure.

Referring to FIG. 3 and FIG. 4, in one embodiment of the base provided by the present disclosure, an air outlet pipe 211 is disposed at the fan 210, and the air outlet pipe 211 is connected to the air outlet 130. After the first airflow and the second airflow flowing to the fan 210 are mixed, the mixed airflow can be driven by the fan 210 and discharged through the air outlet pipe 211. Since the air outlet pipe 211 is connected to the air outlet 130, the mixed airflow can flow through the air outlet pipe 211 and reach the air outlet 130.

Figure 7:
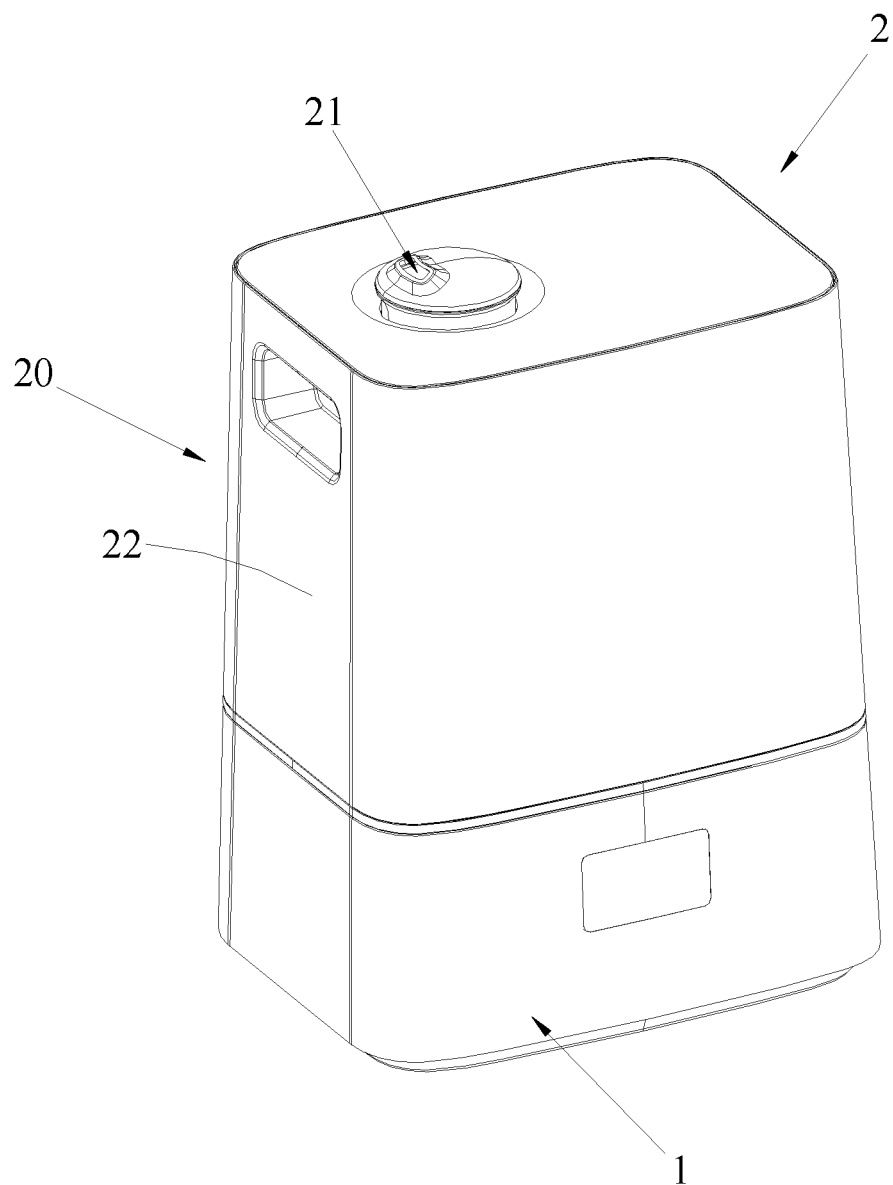
FIG. 7 is a schematic diagram of an overall structure of a humidifier according to an embodiment of the present disclosure.
Figure 8:
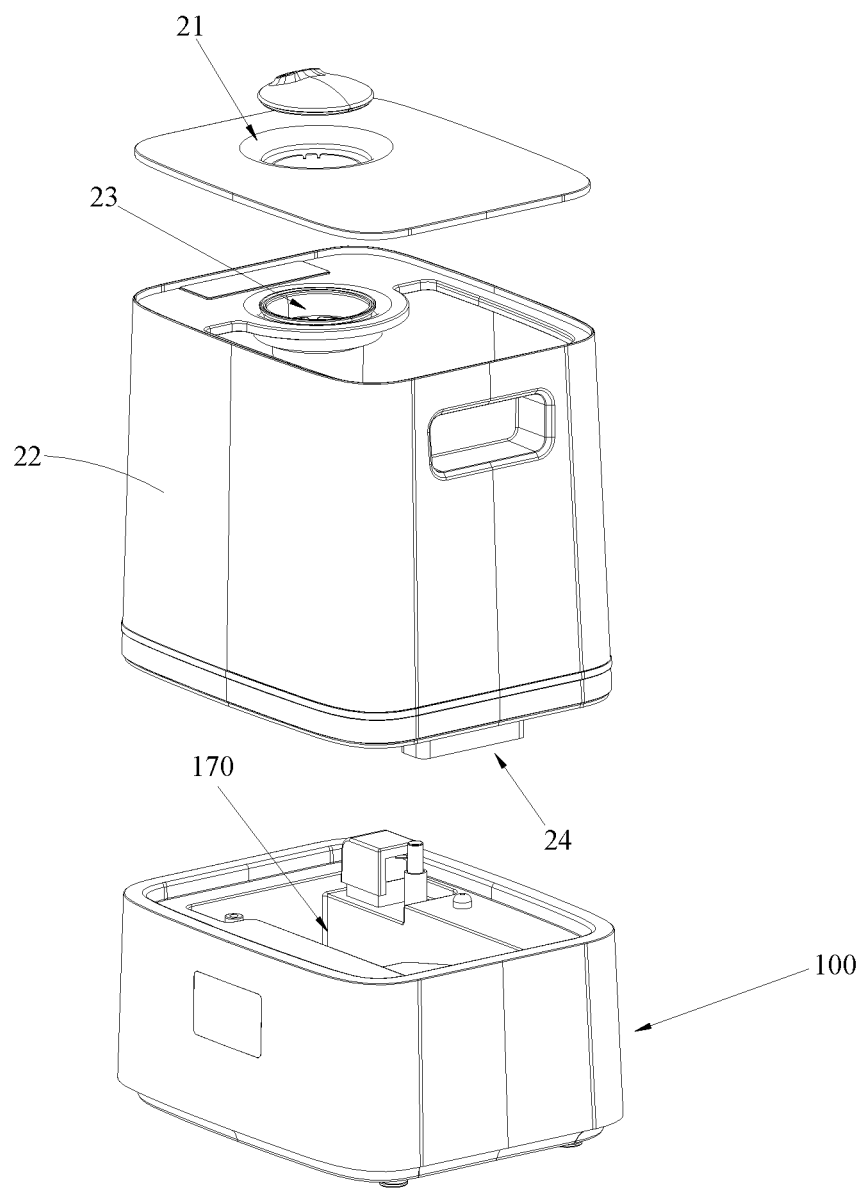
FIG. 8 is an exploded schematic diagram of the humidifier according to an embodiment of the present disclosure.
Figure 9:
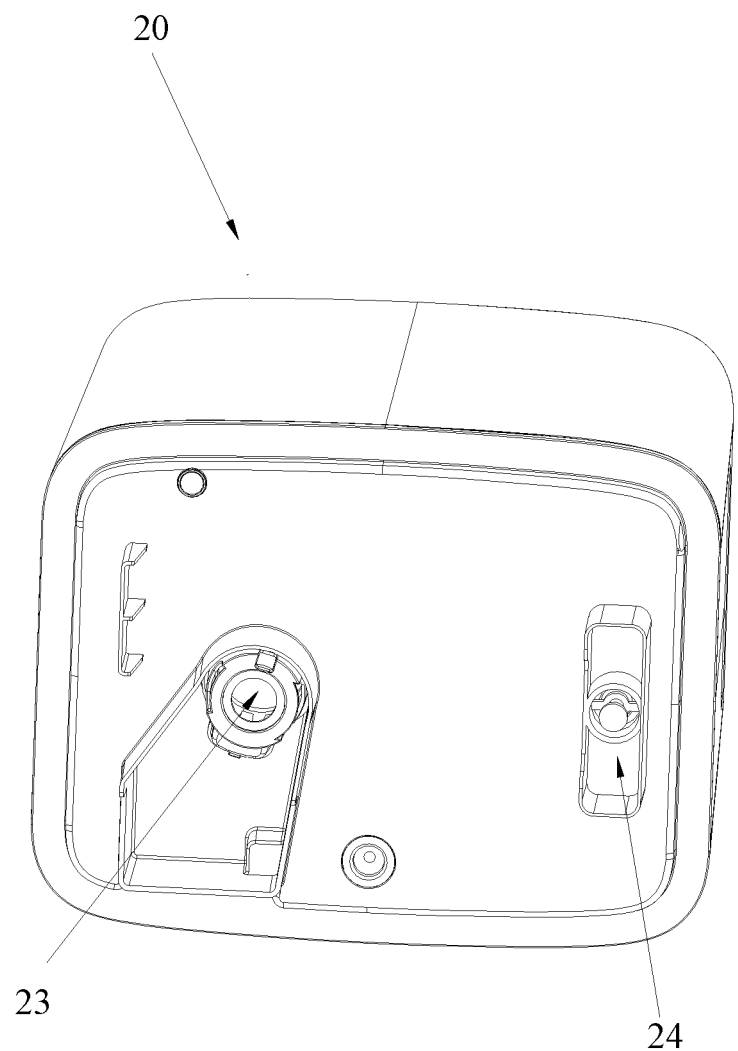
FIG. 9 is a schematic diagram of a water tank according to an embodiment of the present disclosure.

Referring to FIG. 7 to FIG. 9, an embodiment of the present disclosure further provides a humidifier 2. The humidifier 2 includes a water tank 20, a misting assembly 30, and the base 1 described above. The water tank 20 can be detachably mounted on the base 1. The water tank 20 includes a water storage tank 22 and a mist outlet channel 23. The water tank 20 further includes a mist outlet 21 and a water outlet 24. The mist outlet channel 23 is connected to the mist outlet 21 and the air outlet 130.

In some embodiments, the housing 100 further includes a water storage chamber 170 which is connected to the mist outlet channel 23 and the air outlet 130. The water storage chamber 170 connects to the water storage tank 22 through the water outlet 24. The misting assembly 30 can be disposed in the receiving chamber 110 to atomize the water stored in the water storage chamber 170.

An exemplary atomization process is described below. The water stored in the water storage tank 22 flows to the water storage chamber 170 in the housing 100 through the water outlet 24, and the water in the water storage chamber 170 can be converted into water mist under the action of the misting assembly 30. Since the water storage chamber 170 is connected to the air outlet 130, the water mist in the water storage chamber 170 is driven by the mixed airflow blown from the air outlet 130 to the mist outlet channel 23, and then discharged out of the mist outlet 21.

The above descriptions only illustrate some embodiments of the present disclosure. The present disclosure is not limited the described embodiments. A person having ordinary skill in the art may conceive various equivalent modifications or replacements based on the disclosed technology. Such modification or improvement also fall within the scope of the present disclosure. A true scope and spirit of the present disclosure are indicated by the following claims.

What is claimed is:

1. A base of a humidifier comprising:
a housing including a receiving chamber, an air outlet, a first air inlet, and a second air inlet;
an air outlet assembly disposed in the receiving chamber, the air outlet assembly including a fan, a temperature and humidity sensor configured to measure a first airflow introduced from the first air inlet, and an aroma component configured to aromatize a second airflow introduced from the second air inlet; and
a first partition disposed in the receiving chamber and configured to spatially separate the temperature and humidity sensor from the fan and the aroma component,
wherein the fan is configured to: introduce the first airflow from the first air inlet to pass through the temperature and humidity sensor, flow through a ventilation opening at the first partition, and reach the fan; introduce the second airflow flow from the second air inlet to pass through the aroma component without passing through the temperature and humidity sensor, and reach the fan; and discharge the first airflow and the second airflow out of the receiving chamber through the air outlet.

2. The base of the humidifier according to claim 1, wherein: a total opening area of the first air inlet is smaller than a total opening area of the second air inlet.

3. The base of the humidifier according to claim 1, wherein: the first partition fixedly is connected to the housing.

4. The base of the humidifier according to claim 3, further comprising:
a second partition disposed in the receiving chamber and respectively connected to the housing and the first partition; and
a control assembly disposed in the receiving chamber and configured to perform atomization control on liquid of the humidifier, wherein the fan and the aroma component are disposed on one side of the second partition, and the control assembly is disposed on another side of the second partition.

5. The base of the humidifier according to claim 4, wherein: the control assembly is further configured to control a display of the humidifier.

6. The base of the humidifier according to claim 4, wherein:
the housing includes an upper housing and a bottom cover connected to a bottom of the upper housing;
the upper housing and the bottom cover jointly enclose to form the receiving chamber;
the first partition and the second partition divide the receiving chamber into a first flow channel, a second flow channel, and an accommodating chamber;
the first partition and the housing jointly enclose to form the first flow channel, the temperature and humidity sensor being positioned in the first flow channel;
the second partition, the housing, and the first partition jointly enclosing to form the second flow channel;
the aroma component and the fan are positioned in the second flow channel; and
the control assembly is disposed in the accommodating chamber.

7. The base of the humidifier according to claim 6, wherein:
the first air inlet and the second air inlet are both disposed on the bottom cover;
the first air inlet is disposed on the bottom cover at a position corresponding to the temperature and humidity sensor;
the second air inlet is disposed on the bottom cover at a position corresponding to the fan and the aroma component; and
the air outlet is disposed on the upper housing.

8. The base of the humidifier according to claim 7, wherein: the housing further includes a first guiding plate connected to the bottom cover and recessed at the first air inlet, and a second guiding plate connected to the bottom cover and recessed at the second air inlet.

9. The base of the humidifier according to claim 1, wherein: the aroma component is disposed at a position close to the fan and away from the temperature and humidity sensor.

10. The base of the humidifier according to claim 1, wherein: the ventilation opening at the first partition is a ventilation hole or a ventilation channel.

11. A humidifier comprising: a water tank including a water storage tank, a mist outlet channel, a mist outlet, and a water outlet; a misting assembly; and a base comprising:
a housing including a receiving chamber, an air outlet, a first air inlet, a second air inlet, and a water storage chamber;
an air outlet assembly disposed in the receiving chamber and including a fan, a temperature and humidity sensor configured to measure a first airflow introduced from the first air inlet, and an aroma component configured to aromatize a second airflow introduced from the second air inlet; and
a first partition disposed in the receiving chamber and configured to spatially separate the temperature and humidity sensor from the fan and the aroma component,
wherein: the fan is configured to introduce the first airflow from the first air inlet to pass through the temperature and humidity sensor, flow through a ventilation opening at the first partition, and reach the fan; introduce the second airflow flow from the second air inlet to pass through the aroma component without passing through the temperature and humidity sensor, and reach the fan; and discharge the first airflow and the second airflow out of the receiving chamber through the air outlet; the water tank is configured to be detachably mounted to the base; the mist outlet channel, the mist outlet and the air outlet are connected; the water storage chamber of the housing is connected to the mist outlet channel of the water tank and the air outlet of the base, and is connected to the water storage tank through the water outlet; and the misting assembly is positioned in the receiving chamber and configured to atomize water stored in the water storage chamber.

12. The humidifier according to claim 11, wherein: a total opening area of the first air inlet is smaller than a total opening area of the second air inlet.

13. The humidifier according to claim 11, wherein: the first partition fixedly is connected to the housing.

14. The humidifier according to claim 13, wherein the base further comprises:
a second partition disposed in the receiving chamber and respectively connected to the housing and the first partition; and
a control assembly disposed in the receiving chamber and configured to perform atomization control on liquid of the humidifier, wherein the fan and the aroma component are disposed on one side of the second partition, and the control assembly is disposed on another side of the second partition.

15. The humidifier according to claim 14, wherein: the control assembly is further configured to control a display of the humidifier.

16. The humidifier according to claim 14, wherein:
the housing includes an upper housing and a bottom cover connected to a bottom of the upper housing;
the upper housing and the bottom cover jointly enclose to form the receiving chamber;
the first partition and the second partition divide the receiving chamber into a first flow channel, a second flow channel, and an accommodating chamber;
the first partition and the housing jointly enclose to form the first flow channel, the temperature and humidity sensor being positioned in the first flow channel;
the second partition, the housing, and the first partition jointly enclosing to form the second flow channel;
the aroma component and the fan are positioned in the second flow channel; and
the control assembly is disposed in the accommodating chamber.

17. The humidifier according to claim 16, wherein: the first air inlet and the second air inlet are both disposed on the bottom cover; the first air inlet is disposed on the bottom cover at a position corresponding to the temperature and humidity sensor; the second air inlet is disposed on the bottom cover at a position corresponding to the fan and the aroma component; and the air outlet is disposed on the upper housing.

18. The humidifier according to claim 17, wherein: the housing further includes a first guiding plate connected to the bottom cover and recessed at the first air inlet, and a second guiding plate connected to the bottom cover and recessed at the second air inlet.

19. The humidifier according to claim 11, wherein: the aroma component is disposed at a position close to the fan and away from the temperature and humidity sensor.

20. The humidifier according to claim 11, wherein: the ventilation opening at the first partition is a ventilation hole or a ventilation channel.

* * * * *